(12) United States Patent
Seki et al.

(10) Patent No.: US 7,335,778 B2
(45) Date of Patent: Feb. 26, 2008

(54) INTERMEDIATE FOR BIOTIN AND PROCESS FOR PRODUCING THE SAME

(75) Inventors: Masahiko Seki, Kyoto (JP); Toshiaki Shimizu, Osaka (JP); Shin-ichi Yoshida, Hyogo (JP); Masanori Hatsuda, Shiga (JP)

(73) Assignee: Tanabe Seiyaku Co., Ltd., Osaka-shi (JP)

( * ) Notice: Subject to any disclaimer, the term of this patent is extended or adjusted under 35 U.S.C. 154(b) by 388 days.

(21) Appl. No.: 10/496,660

(22) PCT Filed: Dec. 4, 2002

(86) PCT No.: PCT/JP02/12694

§ 371 (c)(1),
(2), (4) Date: May 25, 2004

(87) PCT Pub. No.: WO03/048131

PCT Pub. Date: Jun. 12, 2003

(65) Prior Publication Data

US 2005/0038260 A1    Feb. 17, 2005

(30) Foreign Application Priority Data

Dec. 4, 2001  (JP) .............................. 2001-369479
Jul. 18, 2002  (JP) .............................. 2002-209121

(51) Int. Cl.
*C07D 233/20* (2006.01)
*C07D 277/10* (2006.01)

(52) U.S. Cl. .................................. 548/323.5; 548/189

(58) Field of Classification Search ................ 548/189, 548/323.5
See application file for complete search history.

(56) References Cited

U.S. PATENT DOCUMENTS 5,095,118 A    3/1992    Poetsch et al.

FOREIGN PATENT DOCUMENTS

| EP | 0242686 A | 10/1987 |
|---|---|---|
| EP | 1127879 A | 8/2001 |
| JP | 2000-191665 A | 7/2000 |
| JP | 2001-2679 A | 1/2001 |

OTHER PUBLICATIONS

T. Shimizu et al., XP004212506, Tetrahedron Letters, vol. 41, No. 26, pp. 5099-5101 (2000).

T. Shimizu et al., XP004313721, Tetrahedron Letters, vol. 42, No. 3, pp. 429-432 (2001).
Jackson et al., J.Org. Chem., vol. 63, No. 22, p. 7875-7884 (1998).
Toshiaki Shimizu et al., *Tetrahedron Letters*, vol. 41, (2000), pp. 5099-5101.
Toshiaki Shimizu et al., *Tetrahedron Letters*, vol. 42, (2001), pp. 429-432.
Yakugaku Zasshi, Voll 88, No. 8, (1968), pp. 1062-1067. Isaka et al.

*Primary Examiner*—Rebecca Anderson
*Assistant Examiner*—Jason M Nolan
(74) *Attorney, Agent, or Firm*—Birch, Stewart, Kolasch & Birch, LLP

(57) ABSTRACT

The present invention is to provide a process for preparing a synthetic intermediate of biotin which is industrially advantageous, and discloses a process for preparing a compound represented by the formula (I):

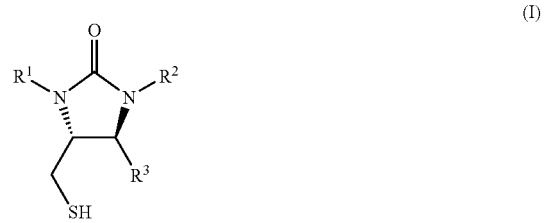

wherein $R^1$ and $R^2$ may be the same or different from each other, and each represents hydrogen atom, a benzyl group which may have a substituent(s) on the benzene ring, a benzhydryl group which may have a substituent(s) on the benzen ring, or a trityl group which may have a substituent(s) on the benzene ring, $R^3$ represents cyano group, carboxyl group, an alkoxycarbonyl group, an alkylthiocarbonyl group, or a carbamoyl group which may have a substituent, or a salt thereof which comprises subjecting a compound represented by the formula (II-a):

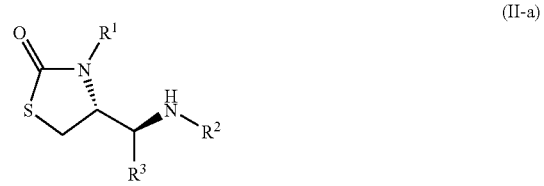

wherein the symbols have the same meanings as defined above,
or a salt thereof to ring transformation.

4 Claims, No Drawings

INTERMEDIATE FOR BIOTIN AND PROCESS FOR PRODUCING THE SAME

TECHNICAL FIELD

The present invention relates to a biotin synthetic intermediate and a process for preparing the same, and a process for preparing biotin using said intermediate.

BACKGROUND ART

Biotin is a vitamine useful as an additive for feed, medicine, etc., and as a process for preparing the same, it has been known a process, for example, in which a thienoimidazol compound represented by the following formula:

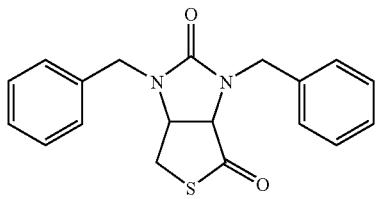

is used as a synthetic intermediate (Chemical Reviews, vol. 97, No. 6, pp. 1755-1792, 1997, Japanese Patent Publications No. Sho. 49-32551 and Sho. 53-27279, Japanese Patent Publications No. Hei. 3-66312 and Hei. 5-9064) and the like.

However, these conventionally known processes involve the problems that its preparation steps are long, and they require complicated optical resolution in the course of the preparation steps.

An object of the present invention is to provide a process for preparing biotin which is industrially advantageous.

DISCLOSURE OF THE INVENTION

To solve the problems, the present inventors have earnestly studied, and as a result, they have found that a process for preparing biotin through Compound (I) and Compound (III) or di(imidazolydinylmethyl)disulfice compound (IV) as a synthetic intermediate can give the above-mentioned thienoimidazole compound inexpensively, so that this is an industrially excellent preparation process, whereby they have accomplished the present invention.

That is, the present invention relates to a process for preparing a compound represented by the formula (I):

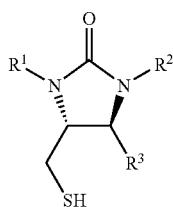

wherein $R^1$ and $R^2$ may be the same or different from each other, and each represents hydrogen atom, a benzyl group which may have a substituent(s) on the benzene ring, a benzhydryl group which may have a substituent(s) on the benzen ring, or a trityl group which may have a substituent(s) on the benzene ring, $R^3$ represents cyano group, carboxyl group, an alkoxycarbonyl group, an alkylthiocarbonyl group, or a carbamoyl group which may have a substituent, or a salt thereof, which comprises subjecting a compound represented by the formula (II-a):

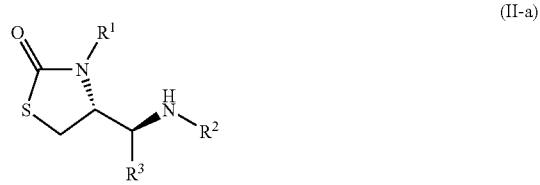

wherein the symbols have the same meanings as defined above, or a salt thereof to ring transformation.

Also, the present invention relates to a process for preparing a compound represented by the formula (III):

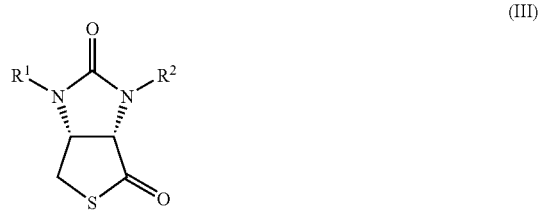

wherein the symbols have the same meanings as defined above, which comprises preparing a compound represented by the formula (I):

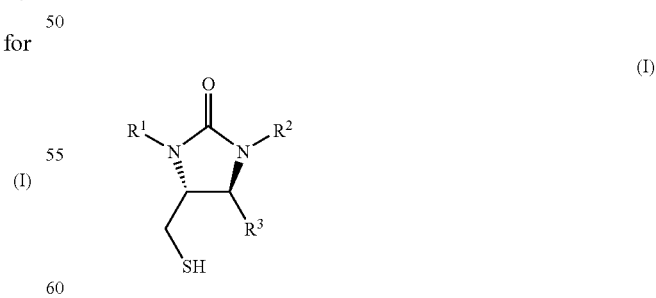

wherein the symbols have the same meanings as defined above, or a salt thereof according to the above-mentioned process, subjecting to hydrolysis, depending on necessity to prepare a compound represented by the formula (I-a):

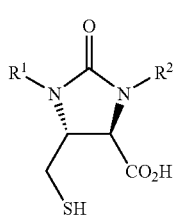
(I-a)

wherein the symbols have the same meanings as defined above, or a salt thereof, and then, subjecting the obtained Compound (I-a) to cyclization and epimerization.

The present invention also relates to a process for preparing a compound represented by the formula (IV):

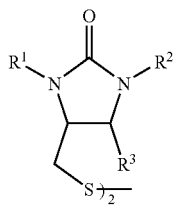
(IV)

wherein the symbols have the same meanings as defined above, which comprises subjecting a compound represented by the formula (II):

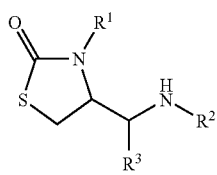
(II)

wherein the symbols have the same meanings as defined above, or a salt thereof to ring transformation and cyclization.

The present invention also relates to a process for preparing a compound represented by the formula (III):

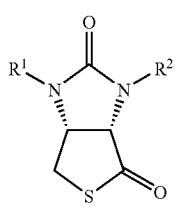
(III)

wherein the symbols have the same meanings as defined above, which comprises reducing a compound represented by the formula (IV-a):

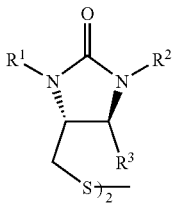
(IV-a)

wherein the symbols have the same meanings as defined above, or a salt thereof according to the above-mentioned method, subjecting to hydrolysis depending on necessity, to prepare a compound represented by the formula (I-a):

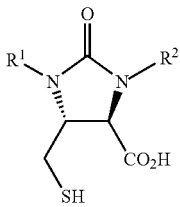
(I-a)

wherein the symbols have the same meanings as defined above, or a salt thereof, and then, subjecting the resulting Compound (I-a) to cyclization and epimerization.

Also, the present invention relates to a process for preparing a compound represented by the formula (III):

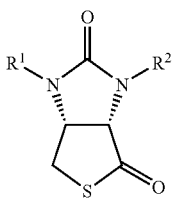
(III)

wherein the symbols have the same meanings as defined above, which comprises subjecting a compound represented by the formula (II-b):

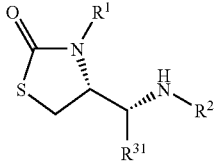
(II-b)

wherein $R^{31}$ represents carboxyl group, an alkoxycarbonyl group, an alkylthiocarbonyl group, or a carbamoyl group which may have a substituent(s), and other symbols have the same meanings as defined above, or a salt thereof to ring transformation and cyclization.

The present invention also relates to a process for preparing a compound represented by the formula (6-a):

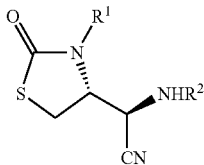

(6-a)

wherein the symbols have the same meanings as defined above, or a salt thereof, which comprises reacting a compound represented by the formula (5-a):

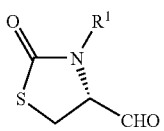

(5-a)

wherein the symbol has the same meaning as defined above, or a salt thereof with a compound represented by the formula (7):

$R^2$—$NH_2$ (7)

wherein the symbol has the same meaning as defined above, and a cyanide compound.

The present invention further relates to a process for preparing a compound represented by a compound represented by the formula (6-a):

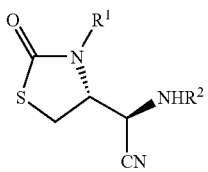

(6-a)

wherein the symbols have the same meanings as defined above, or a salt thereof, which comprises oxidizing a compound represented by the formula (4-a):

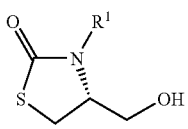

(4-a)

wherein the symbol has the same meaning as defined above, or a salt thereof to prepare a compound represented by the formula (5-a)

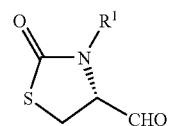

(5-a)

wherein the symbol has the same meaning as defined above, or a salt thereof, and then, reacting the resulting Compound (5-a) with a compound represented by the formula (7):

$R^2$—$NH_2$ (7)

wherein the symbol has the same meaning as defined above, and a cyanide compound.

The present invention further relates to a process for preparing a compound represented by a compound represented by the formula (III):

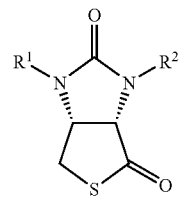

(III)

wherein the symbols have the same meanings as defined above, which comprises preparing a compound represented by the formula (6-a):

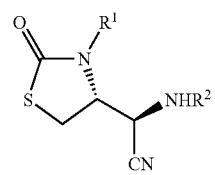

(6-a)

wherein the symbols have the same meanings as defined above, or a salt thereof according to the above-mentioned method, subjecting the resulting Compound (6-a) to hydrolysis to prepare a compound represented by the formula (II-c):

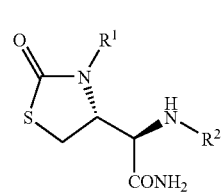

(II-c)

wherein the symbols have the same meanings as defined above, then, subjecting the resulting Compound (II-c) to ring transformation to prepare a compound represented by the formula (I-b):

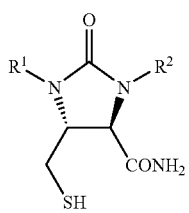

(I-b)

wherein the symbols have the same meanings as defined above, or a salt thereof, subjecting the resulting Compound (I-b) to hydrolysis to prepare a compound represented by the formula (I-a):

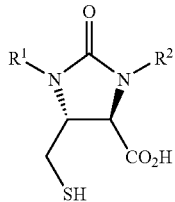

(I-a)

wherein the symbols have the same meanings as defined above, or a salt thereof, and subjecting the resulting compound (I-a) to cyclization and epimerization.

Further, the present invention relates to a process for preparing a compound represented by a compound represented by the formula (VII):

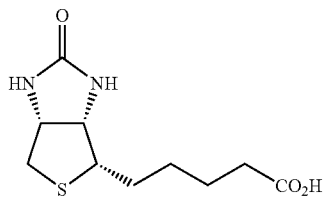

(VII)

which comprises preparing a compound represented by the formula (III):

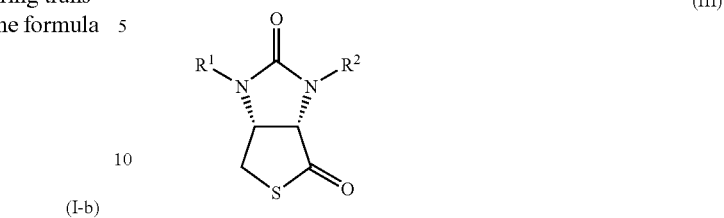

(III)

wherein the symbols have the same meanings as defined above, according to the above-mentioned method, reacting the resulting Compound (III) with a compound represented by the formula (V):

$X^1Zn—(CH_2)_4R^4$ (V)

wherein $X^1$ represents a halogen atom, and $R^4$ represents an esterified carboxyl group or an amidated carboxyl group, to give a compound represented by the formula (VI):

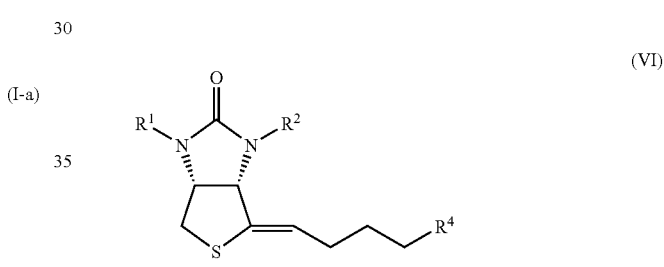

(VI)

wherein the symbols have the same meanings as defined above, or a salt thereof, then, reducing the resulting Compound (VI), and subjecting it to hydrolysis, if necessary, and further converting $R^1$ and/or $R^2$ to hydrogen atom, if necessary.

Moreover, the present invention relates to a di(imidazolidinylmethyl)disulfide compound represented by the formula (IV):

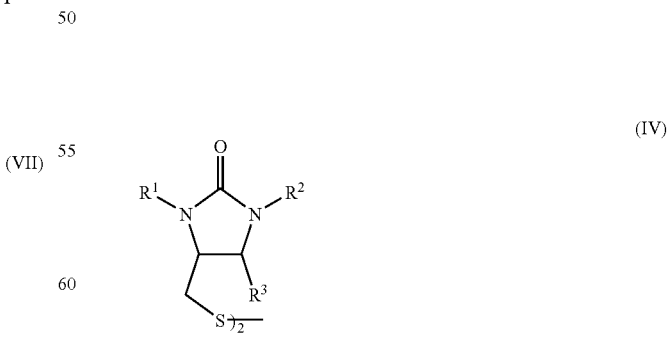

(IV)

wherein the symbols have the same meanings as defined above, or a salt thereof.

Moreover, the present invention relates to a process for preparing a compound represented by a compound represented by the formula (IX):

R—X—Y     (IX)

wherein X represents zinc or magnesium, and Y represents iodine, bromine or chlorine, which comprises reacting a compound represented by the formula (VIII):

R—I     (VIII)

wherein R represents an alkyl group which may have a substituent(s), a bicyclo group which may have a substituent(s), an alkenyl group which may have a substituent(s), a heterocyclic group which contains 1 to 4 atoms selected from nitrogen atom, oxygen atom and sulfur atom as a hetero atom(s) (said heterocyclic group may have a substituent(s)) or an aryl group which may have a substituent(s), with zinc or magnesium which has been treated by chlorine, bromine, hydrogen chloride or hydrogen bromide.

Also, the present invention further relates to a process for preparing a compound represented by a compound represented by the formula (IX):

R—X—Y     (IX)

wherein the symbols have the same meanings as defined above, which comprises reacting a compound represented by the formula (VIII):

R—I     (VIII)

wherein R has the same meaning as defined above, with zinc or magnesium in the presence of a salt represented by the formula (X):

M-Y     (X)

wherein M represents a metal atom, Y has the same meaning as defined above.

BEST MODE FOR CARRYING OUT THE INVENTION

Compound (I) to be used or obtained in the present invention can be obtained by subjecting Compound (II-a) to ring transformation. This reaction can be carried out in the absence of oxygen, for example, under nitrogen or argon atmosphere, etc. This reaction can be carried out in a suitable solvent or in the absence of a solvent. As the solvent, any solvent which does not cause any unfavorable effect to the reaction may be used, and there may be preferably used, for example, N,N-dimethylformamide, dimethylsulfoxide, N,N-dimethylacetamide, N-methyl-2-pyrrolidone or a mixed solvent of the above-mentioned solvents. The present reaction preferably proceeds at 0° C. to 200° C., particularly preferably at 80° C. to 100° C.

In $R^1$ and $R^2$ of Compound (I), Compound (I-a), Compound (I-a'), Compound (I-b), Compound (II), Compound (II'), Compound (II-a), Compound (II-b), Compound (II-c), Compound (III), Compound (III-a), Compound (IV), Compound (IV-a), Compound (VI), Compound (6) and Compound (6-a) to be used or obtained in the present invention, and in $R^1$ of Compound (3), Compound (4), Compound (4-a), Compound (5) and Compound (5-a) to be used or obtained in the present invention, and in $R^2$ of Compound (7), as a substituent(s) on the benzene ring of the benzyl group, a group selected from a halogen atom, an alkyl group and an alkoxy group may be mentioned, and as a substituent(s) on the benzene ring of the benzhydryl group, the same or different group(s) selected from a halogen atom, an alkyl group and an alkoxy group may be mentioned, and as a substituent(s) on the benzene ring of the trityl group, the same or different group(s) selected from a halogen atom, an alkyl group and an alkoxy group may be mentioned.

On the respective benzene rings of the above-mentioned benzyl group, benzhydryl group or trityl group, the same or different 1 to 3 above-mentioned substituent(s) may be substituted.

In $R^3$ of Compound (I), Compound (II), Compound (II-a), Compound (IV) and Compound (IV-a) to be used or obtained in the present invention and in $R^{31}$ of Compound (II-b), as a substituent(s) for a carbamoyl group, the same or different 1 or 2 alkyl group(s) may be mentioned.

As Compound (I), Compound (I-a), Compound (I-a'), Compound (I-b), Compound (II), Compound (II'), Compound (II-a), Compound (II-b), Compound (II-c), Compound (III), Compound (III-a), Compound (IV), Compound (IV-a), Compound (VI), Compound (6) and Compound (6-a) to be used or obtained in the present invention, a compound in which $R^1$ and $R^2$ are both benzyl groups, benzhydryl groups or trityl groups is preferred. Of these, particularly preferred is a compound in which $R^1$ and $R^2$ are both benzyl groups. Also, as Compound (I), Compound (II), Compound (II-a), Compound (IV) and Compound (IV-a), a compound in which $R^3$ is carboxyl group, an alkoxycarbonyl group or a carbamoyl group is preferred.

Compound (IV) to be used or obtained in the present invention can be prepared by subjecting Compound (II) to ring transformation in the presence of a base.

As a base, there may be preferably used an alkali metal carbonate (sodium carbonate, potassium carbonate, etc.), an alkali metal hydrogen carbonate (sodium hydrogen carbonate, etc.), an organic acid alkali metal salt (sodium acetate, etc.), an alkali metal hydroxide (sodium hydroxide, potassium hydroxide, etc.), an alkali metal hydride (sodium hydride, etc.), an alkali metal amide (sodium amide, lithium amide, etc.), an alkali metal alkoxide (sodium methoxide, etc.), an alkali metal phosphate, an alkali metal (sodium, etc.) or an organic base (triethylamine, diisopropylethylamine, morpholine, N-methylmorpholine, pyridine, piperidine, dimethylaniline, dimethylaminopyridine, etc.) and the like. Of these, sodium hydrogen carbonate or sodium acetate is particularly preferred.

An amount of the base to be used is preferably 0.1 molar equivalent to 100 molar equivalent, particularly 1 molar equivalent to 3 molar equivalent based on the amount of Compound (II).

This reaction can be carried out in a suitable solvent or in the absence of a solvent. As the solvent, any solvent which does not cause any unfavorable effect to the reaction may be used, and there may be preferably used, for example, N,N-dimethylformamide, dimethylsulfoxide, N,N-dimethylacetamide, N-methylpyrrolidine or a mixed solvent of the above-mentioned solvents. The present reaction preferably proceeds at 0 to 200° C., particularly preferably at 80 to 100° C.

In Compound (IV) to be used in the present invention, optical isomers based on an asymmetric carbon exist, and it may be either a racemic mixture or an optical isomer. Of these, an optically active (+)-biotin alone has biological activity, so that an optical isomer in which 5-position (the position to which —CH₂S— binds) of the imidazolidine ring is an R configuration is preferred to lead it to (+)-biotin with good efficiency.

As Compound (VI) to be used or obtained in the present invention, a compound in which $R^1$ and $R^2$ are both benzyl groups, benzhydryl groups or trityl groups, and $R^4$ is an alkoxycarbonyl group or an alkylcarbamoyl group is preferred. Of these, particularly preferred is a compound in which $R^1$ and $R^2$ are both benzyl groups, benzhydryl groups or trityl groups, and $R^4$ is an alkoxycarbonyl group.

Compound (II) and Compound (II-a) can be prepared by conventionally known methods described in Bulletin of Chemical Society of Japan, vol. 37., No. 2, pp. 242-244, 1964, Analytical Biochemistry, vol. 138, pp. 449-450, 1984, Heterocycles, vol. 18, pp. 259-263, 1982, etc. or methods in accordance with the above methods, and, for example, these compounds can be prepared as follows.

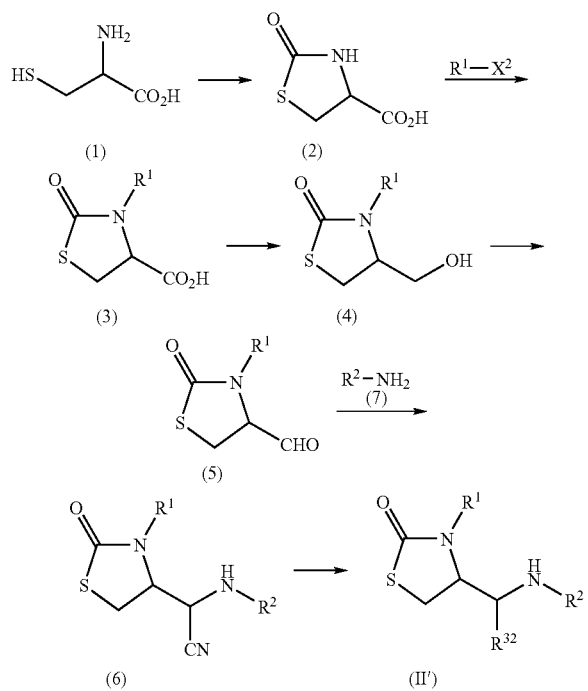

wherein $X^2$ represents a halogen atom, $R^{32}$ represents carboxyl group or a carbamoyl group, and other symbols have the same meanings as defined above.

The step of producing Compound (2) from Compound (1) and phenyl chloroformate (or alkyl chloroformate) can be carried out in the presence of a base in a solvent or in the absence of a solvent. As the base, there may be preferably used an alkali metal hydroxide, an alkali metal carbonate, an alkali metal hydrogen carbonate, an alkali metal alkoxide, an organic base, etc. As the solvent, any solvent which does not cause any unfavorable effect to the reaction may be used, and there may be mentioned, for example, toluene, benzene, xylene tetrahydrofuran, 1,4-dioxane, diethyl ether, dichloromethane, water, etc. The present reaction preferably proceeds at −30° C. to 120° C., particularly preferably at 20° C. to 50° C.

In Compound (3), a compound in which $R^1$ has a substituent other than hydrogen atom can be prepared by reacting Compound (2) and $R^1$—$X^2$ (chloride, bromide, etc. of $R^1$) in the presence of a base and a high polar solvent such as dimethylsulfoxide, etc., in a solvent or in the absence of a solvent. As the base, there may be preferably used an alkali metal hydroxide, an alkali metal carbonate, an alkali metal hydrogen carbonate, an alkali metal alkoxide, an organic base, etc. As the solvent, any solvent which does not cause any unfavorable effect to the reaction may be used, and there may be mentioned, for example, water, N,N-dimethylformamide, N,N-dimethylacetamide, N-methyl-2-pyrrolidone, methanol, etc. The present reaction preferably proceeds at −20° C. to 120° C., particularly preferably at 15° C. to 40° C.

Compound (4) can be produced by reacting Compound (3) with a reducing agent, in the presence of an acid or an alkylating agent, in a solvent or in the absence of a solvent. As the reducing agent, there may be preferably used sodium borohydride, lithium borohydride, lithium aluminum hydride, Red-Al (bis(2-methoxyethoxy)aluminum sodium hydride), diborane, borane methylsulfide complex, etc. As the acid, there may be preferably used sulfuric acid, hydrogen chloride, a Lewis acid (trimethylsilyl chloride, iodine, chlorine, borane trifluoride ether complex, etc.), etc. As the alkylating agent, there may be preferably used dimethyl sulfate, methyl iodide, benzyl halide, etc. As the solvent, any solvent which does not cause any unfavorable effect to the reaction may be used, and there may be mentioned, for example, tetrahydrofuran, ethanol, etc. The present reaction preferably proceeds at −30° C. to 120° C., particularly preferably at 0° C. to 40° C.

Compound (5) can be produced by reacting Compound (4) in the presence of an oxidizing agent, in a solvent or in the absence of a solvent. As the oxidizing agent, there may be preferably used (1) that comprising dimethylsulfoxide, sulfur trioxide pyridine complex salt and an amine (diisopropylethylamine, triethylamine, etc.), (2) that comprising dimethylsulfoxide, oxalyl chloride and an amine (diisopropylethylamine, triethylamine, etc.), (3) that comprising dimethylsulfide, chlorine and an amine (diisopropylethylamine, triethylamine, etc.), (4) that comprising sodium hypochlorite, sodium hydrogen carbonate, sodium bromide, and 4-hydroxytetramethylpiperidineoxide or its derivative (4-aminotetramethylpiperidineoxide, 4-carboxytetramethylpiperidineoxide, 4-cyanotetramethylpiperidineoxide, etc.), (5) chromic acid and its salt, (6) a metal catalyst (platinum, palladium, etc.) and oxygen, (7) a peracid and a peroxide, or (8) dimethylsulfoxide, DCC (dicyclohexylcarbodiimide), a base (pyridine, etc.), an acid (trifluoroacetic acid, phosphoric acid, etc.) (Pfitzner-Moffatt oxidation) and the like. As the solvent, any solvent which does not cause any unfavorable effect to the reaction may be used, and there may be mentioned, for example, dimethylsulfoxide, dichloromethane, water, benzene, toluene, etc. The present reaction preferably proceeds at −78° C. to 100° C., particularly preferably at −78° C. to 25C.

Also, Compound (5) can be also prepared by halogenating the carboxyl group of Compound (3) with thionyl chloride, oxalyl chloride, etc., then subjecting to catalytic reduction by using a metal catalyst (platinum, palladium, etc.) and hydrogen, without through Compound (4).

Compound (6) can be prepared by carrying out a step of reacting Compound (5) with $R^2$—$NH_2$ and step of reacting with a cyanide compound in a solvent or in the absence of a solvent. The reaction of Compound (5) and $R^2$—$NH_2$ can be preferably carried out by reacting them with a cyanide compound in the presence of a dehydrating agent (Molecular Sieves 4A, magnesium sulfate, sodium sulfate, etc.). The cyanide compound is a compound which is usually used when cyanation is carried out, and there may be mentioned, for example, hydrocyanic acid, alkali metal cyanide or organic cyanide, etc., and of these, an alkali metal cyanide is preferably used. As the alkali metal cyanide compound, there may be mentioned, for example, lithium cyanide, sodium cyanide, potassium cyanide, etc., and as the organic cyanide, there may be mentioned, for example, trimethylsilyl cyanide, tributyl tin cyanide, dimethylaluminum cyanide, tetraethyl ammonium cyanide, etc.

As the solvent, any solvent which does not cause any unfavorable effect to the reaction may be used, and there may be mentioned, for example, dichloromethane, toluene, acetonitrile, acetone, ethyl acetate, diethyl ether, tetrahydrofuran, 1,4-dioxane, etc. The reaction of Compound (5) and $R^2$—$NH_2$ preferably proceeds at −50° C. to 100° C., particularly preferably at 0° C. to 20° C. Also, the step of reacting with a cyanide compound preferably proceeds at −78° C. to 100° C., particularly preferably at −20° C. to 20° C.

Compound (II') can be prepared by using Compound (6) as follows.

Compound (II) wherein $R^3$ is carboxyl group and Compound (II-a) wherein $R^{31}$ is carboxyl group can be prepared by reacting Compound (6) in the presence of an acid or a base in a solvent or in the absence of a solvent. As the acid, sulfuric acid, hydrochloric acid, etc. may be preferably used. As the base, an alkali metal hydroxide, an alkali metal alkoxide, etc. may be preferably used. As the solvent, any solvent which does not cause any unfavorable effect to the reaction may be used, and there may be mentioned, for example, dichloromethane, water, tetrahydrofuran, ethanol, etc. The present reaction preferably proceeds at −30° C. to 200° C., particularly preferably at 0° C. to 100° C.

Compound (II) wherein $R^3$ is a carbamoyl group and Compound (II-a) wherein $R^{31}$ is a carbamoyl group can be prepared by reacting Compound (6) in the presence of an acid in a solvent or in the absence of a solvent, and further neutralizing with a base. As the acid, hydrogen peroxide, hydrochloric acid, sulfuric acid, phosphoric acid, methanesulfonic acid, etc. may be preferably used. As the base, ammonia, monomethylamine, dimethylamine, sodium hydroxide, sodium hydrogen carbonate, sodium carbonate, potassium hydroxide, potassium hydrogen carbonate, potassium carbonate, potassium phosphate, dipotassium hydrogen phosphate, etc. may be preferably used. As the solvent, any solvent which does not cause any unfavorable effect to the reaction may be used, and there may be mentioned, for example, toluene, dichloromethane, tetrahydrofuran, N,N-dimethylformamide, dimethylsulfoxide, 1,4-dioxane, methyl ethyl ketone, acetone, chloroform, 1,2-dichloroethane, xylene, mesitylene, tert-butyl methyl ether, etc. The present reaction preferably proceeds at 0° C. to 100° C., particularly preferably at 30° C. to 50° C.

In the above-mentioned reaction, a combination of aqueous hydrogen peroxide as an acid, potassium carbonate as a base and dimethylsulfoxide as a solvent is preferred.

With regard to Compound (1), Compound (2), Compound (3), Compound (4), Compound (5), Compound (6) and Compound (II') to be used in the present invention, optical isomers based on an asymmetric carbon exist, and it may be either a racemic mixture or an optical isomer. Of these, an optically active (+)-biotin alone has biological activity, so that to lead the compound to (+)-biotin with good efficiency by the process of the present invention, the following respective optical isomers are preferred. Also, a compound wherein $R^{31}$ of Compound (II'-a) is carboxyl group is Compound (II-c).

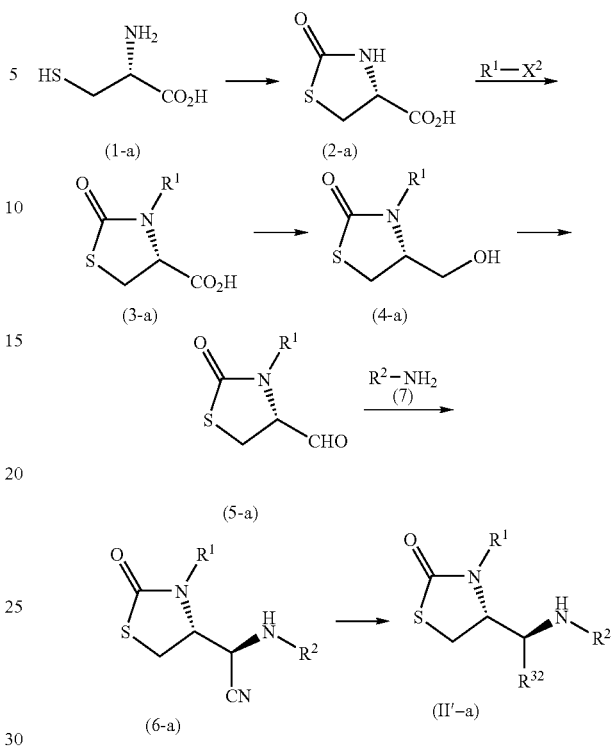

wherein the symbols have the same meanings as defined above.

Also, Compound (4) can be prepared by the conventionally known process as disclosed in Heterocycles, vol. 18, pp. 259-263, 1982, etc. or a method in accordance with the above process, and for example, it may be also prepared as follows.

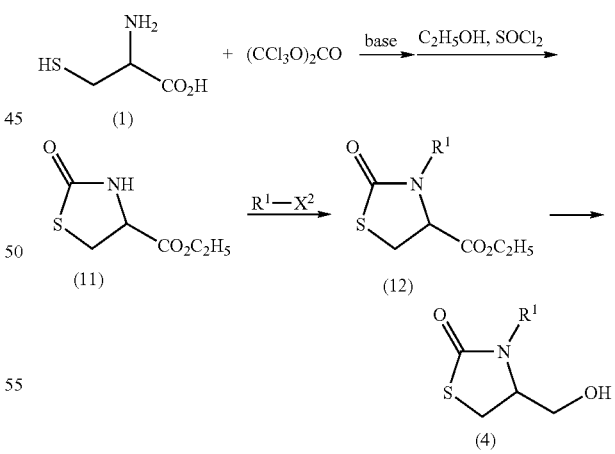

wherein the symbols have the same meanings as defined above.

Compound (11) can be prepared by reacting cysteine and triphosgene (or phosgene, phenyl chloroformate, alkyl chloroformate, etc.) in the presence of a base (an alkali metal hydroxide, an alkali metal carbonate, an alkali metal hydrogen carbonate, etc.) in a solvent or in the absence of a solvent, and further reacting in the presence of ethanol and an activating agent (thionyl chloride, sulfuric acid, hydrogen chloride, oxalyl chloride, etc.). As the solvent, any solvent which does not cause any unfavorable effect to the reaction may be used, and there may be mentioned, for example, water, 1,4-dioxane, tetrahydrofuran, diethyl ether, etc. The present reaction preferably proceeds at −20° C. to 100° C., particularly preferably at 0° C. to 40° C.

In Compound (12), a compound in which $R^1$ has a substituent other than the hydrogen atom can be prepared by reacting Compound (11) and $R^1—X^2$ (chloride, bromide, etc. of $R^1$) in the presence of a base in a solvent or in the absence of a solvent. As the base, an alkali metal carbonate, an alkali metal hydride, an alkali metal amide, etc. As the solvent, any solvent which does not cause any unfavorable effect to the reaction may be used, and there may be mentioned, for example, N,N-dimethylacetamide, acetone, acetonitrile, tetrahydrofuran, etc. The present reaction preferably proceeds at −20° C. to 100° C., particularly preferably at 15° C. to 35° C.

Compound (4) can be prepared by reacting Compound (12) in the presence of a reducing agent in a solvent or in the absence of a solvent. As the reducing agent, sodium borohydride, lithium borohydride, lithium aluminum hydride, Red-Al, DIBAL (diisobutylaluminum hydride), calcium borohydride, zinc borohydride, etc. can be preferably used. As the solvent, any solvent which does not cause any unfavorable effect to the reaction may be used, and there may be mentioned, for example, ethanol, methanol, water, diethyl ether, tetrahydrofuran, 1,4-dioxane, etc. The present reaction preferably proceeds at −78° C. to 50° C., particularly preferably at −20° C. to 20° C.

Also, Compound (5) can be prepared by the conventionally known method as disclosed in J. Am. Chem. Soc., vol. 112, pp. 7050-7051, 1990, etc. or a method in accordance with these processes, and for example, it may be prepared as follows.

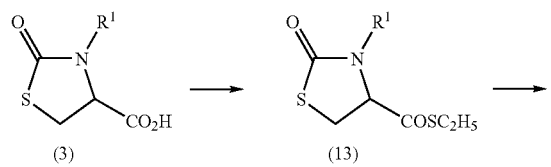

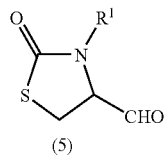

wherein the symbol has the same meanings as defined above.

Compound (13) can be prepared by reacting Compound (3) and ethanethiol in the presence of an activating agent in a solvent or in the absence of a solvent. As the activating agent, DCC, EDC.HCl (1-[3-(dimethylamino)-propyl]-3-ethylcarbodiimide hydrochloride), chlorocarbonates, isocyanuric chloride, CDI (carbonyldiimidazole), etc. may be preferably used. In this reaction, it is more preferred to further add DMAP (1,4-dimethylaminopyridine) since the reaction proceeds rapidly. As the solvent, any solvent which does not cause any unfavorable effect to the reaction may be used, and there may be mentioned, for example, acetonitrile, acetone, tetrahydrofuran, benzene, toluene, etc. The present reaction preferably proceeds at −50° C. to 100° C., particularly preferably at 0° C. to 20° C.

Compound (5) can be prepared by reacting Compound (13) in the presence of a reducing agent and a catalyst in a solvent or in the absence of a solvent. As the reducing agent, silanes such as triethylsilane, trichlorosilane, triphenylsilane, etc. may be preferably used. As the catalyst, palladium catalysts such as palladium hydroxide, palladium carbon, palladium black, etc. may be preferably used. As the solvent, any solvent which does not cause any unfavorable effect to the reaction may be used, and there may be mentioned, for example, dichloromethane, acetone, tetrahydrofuran, etc. The present reaction preferably proceeds at −20° C. to 100° C., particularly preferably at 0° C. to 20° C.

Also, biotin which is the final objective product can be prepared by converting Compound (I) or Compound (II-a) into Compound (III), then, by the conventionally known methods as disclosed in Japanese Unexamined Patent Publications No. Hei. 8-231553 and No. 2000-191665, and Chemical Reviews, vol. 97, No. 6, pp. 1755-1792, 1997, etc. or the method in accordance with these methods, and for example, it may be also prepared as follows.

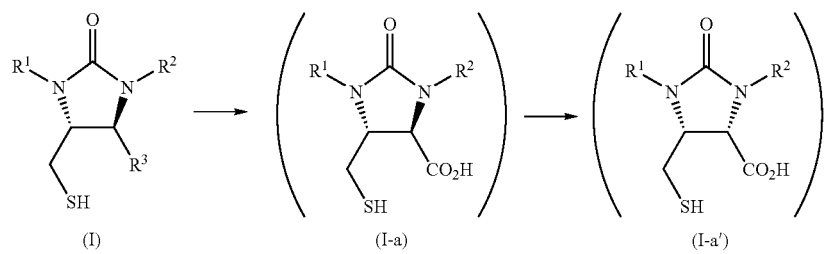

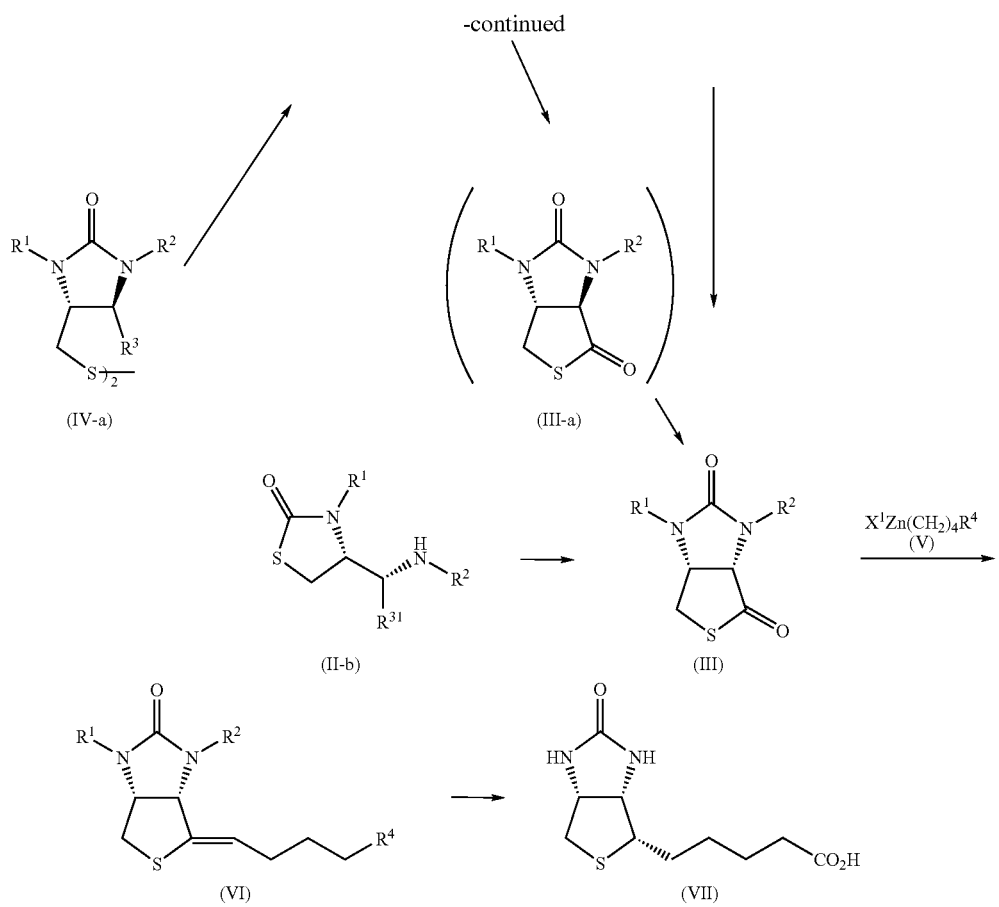

wherein $X^1$ represents a halogen atom, $R^4$ represents an esterified carboxyl group or an amidated carboxyl group, and the other symbols have the same meanings as defined above.

Moreover, in Compound (I), when $R^3$ is cyano group, an alkoxycarbonyl group, an alkylthiocarbonyl group or a carbamoyl group which may have a substituent(s), a conversion of $R^3$ into carboxyl group (Compound (I-a)) can be carried out by the conventional manner as disclosed in, for example, "Basis and Experiment of Peptide Synthesis" written by Nobuo Izumiya et al. (Maruzen Co., Ltd., 1985), or "PROTECTIVE GROUPS IN ORGANIC SYNTHESIS", The Second Edition, written by Greene, et. al., (John Wiley & Sons Co., 1991) or methods in accordance with these methods by hydrolysis. More specifically, for example, it can be converted into carboxyl group by hydrolysis using a base such as an alkali metal hydroxide, an alkali metal alkoxide, etc., an acid such as a mineral acid (hydrochloric acid, sulfuric acid, etc.), etc. As the solvent, any solvent which does not cause any unfavorable effect to the reaction may be used, and there may be mentioned, for example, acetic acid, water, ethanol, tetrahydrofuran, dichloromethane, etc. The present hydrolysis reaction preferably proceeds at 0° C. to 200° C., particularly preferably at 50° C. to 80° C.

Compound (III) can be prepared by subjecting Compound (II-b) to ring transformation and cyclization under a atmosphere, for example, nitrogen or argon, etc. in the absence of oxygen in a solvent or in the absence of a solvent, or subjecting Compound (I-a) or Compound (IV-a) to cyclization and epimerization in a solvent or in the absence of a solvent.

As the solvent to be used in the step of ring transformation and cyclization of Compound (II-b), any solvent which does not cause any unfavorable effect to the reaction may be used, and there may be mentioned, for example, N,N-dimethylformamide, dimethylsulfoxide, N,N-dimethylacetamide, N-methyl-2-pyrrolidone, etc. The present reaction preferably proceeds at 0° C. to 200° C., particularly preferably at 80° C. to 100° C.

The cyclization and epimerization of Compound (I-a) or Compound (IV-a) in the present invention may contain both of the steps of a step in which cyclization is carried out and then epimerization is carried out (a step through Compound (III-a)) and a step in which epimerization is carried out and then cyclization is carried out (a step through Compound (I-a')).

The cyclization step of Compound (I-a) or Compound (IV-a) may be preferably carried out in the presence of an activating agent. As the activating agent, DCC, EDC.HCl, cyanuric chloride, etc. may be preferably used. Also, the cyclization step can be carried out, depending on necessity, in the presence of a base to be used in the epimerization step mentioned below. The epimerization step can be preferably carried out in the presence of a base, or without addition of any additive under heating alone. As the base, an organic base such as pyridine, DBU (1,8-diazabicyclo[5.4.0]undeca-7-ene), triethylamine, etc. may be preferably used. Also, the epimerization step may be carried out, depending on necessity, in the presence of an acid (p-toluenesulfonic acid, hydrogen chloride, etc.).

As the solvent to be used in the cyclization and epimerization step, any solvent which does not cause any unfavorable effect to the reaction may be used, and there may be mentioned, for example, pyridine, toluene, tetrahydrofuran, acetone, acetonitrile, ethanol, etc. The present reaction preferably proceeds at −20° C. to 120° C., particularly preferably at 0° C. to 70° C.

Compound (VI) can be prepared by reacting Compound (III) and Compound (V) in the presence of a catalyst in a solvent or in the absence of a solvent, and then, subjecting to hydrolysis. As the catalyst, palladium hydroxide, palladium carbon, palladium oxide, palladium black, tetrakis triphenylphosphine palladium, dichlorobistriphenylphosphine palladium, etc. may be preferably used. The hydrolysis reaction can be preferably carried out in the presence of water or an acid (p-toluenesulfonic acid, hydrochloric acid, sulfuric acid, etc.). As the solvent, any solvent which does not cause any unfavorable effect to the reaction may be used, and there may be mentioned, for example, tetrahydrofuran, N,N-dimethylformamide, toluene, etc. The present reaction preferably proceeds at −20° C. to 200° C., particularly preferably at 30° C. to 50° C.

Biotin (VII) can be prepared by reducing Compound (VI) in a solvent or in the absence of a solvent, then subjecting to hydrolysis, and when $R^1$ and/or $R^2$ of Compound (VI) is a group other than the hydrogen atom, by further converting (deprotection reaction of the protective group) of said $R^1$ and/or $R^2$ into hydrogen atom.

The reduction can be preferably carried out, for example, by adding hydrogen in the presence of a catalyst such as palladium hydroxide, palladium carbon, palladium black, palladium chloride, palladium acetate, palladium oxide, etc. The hydrolysis reaction can be preferably carried out, for example, by using a base such as sodium hydroxide, etc. As the solvent, any solvent which does not cause any unfavorable effect to the reaction may be used, and there may be mentioned, for example, methanol, ethanol, tetrahydrofuran, water or a mixed solvent of the above-mentioned solvents, etc. The present reaction preferably proceeds at 0° C. to 200° C., particularly preferably at 50° C. to 80° C.

Moreover, when $R^1$ and/or $R^2$ of Compound (VI) is a group other than the hydrogen atom, a step (deprotection reaction of the protective group) of converting said $R^1$ and/or $R^2$ into hydrogen atom can be carried out according to the conventional manner, for example, by the method disclosed in written by Greene, et. al., "PROTECTIVE GROUPS IN ORGANIC SYNTHESIS", The Second Edition (John Wiley & Sons Co., 1991) or a method in accordance with the above method. As a specific example, it can be preferably carried out by treating with a hydrohalogenic acid such as hydrobromic acid, etc., or by treating with mesitylene and an acid (methanesulfonic acid, sulfuric acid, acetic acid, etc.). As the solvent, any solvent which does not cause any unfavorable effect to the reaction may be used, and there may be mentioned, for example, water, benzene, toluene, dichloromethane, etc. The present reaction preferably proceeds at 0° C. to 200° C., particularly preferably at 80° C. to 100° C.

A process for producing Compound (IX) is described in HANDBOOK OF GRIGNARD REAGENTS, pp. 53-77, 1996, ORGANOZINC REAGENTS in ORGANIC SYNTHESIS, pp. 18-67, 1996, etc.

In the present invention, Compound (IX) can be produced more effectively as compared to the methods disclosed in these literatures.

Compound (IX) can be prepared by suspending zinc or magnesium in a solvent, and after adding chlorine, bromine, hydrogen chloride or hydrogen bromide thereto, reacting with Compound (VIII). As the solvent, any solvent which does not cause any unfavorable effect to the reaction may be used, and there may be mentioned, for example, tetrahydrofuran, toluene, diethyl ether, 1,2-dimethoxyethane, acetonitrile, 1,4-dioxane, etc., a mixed solvent of the above-mentioned solvents may be used. The present reaction preferably proceeds at −50° C. to 150° C., particularly preferably at 5° C. to 80° C.

As the substituent for the alkyl group of R, there may be mentioned an alkoxycarbonyl group, an alkoxy group, an alkoxycarbonylalkenyl group, an alkoxycarbonylalkynyl group, an alkanoyl group, an alkylaminocarbonoyl group, an alkynyl group, cyano group, an alkoxycarbamoyl group, an alkylcarbamoyl group, di(alkanoyl)amino group, a halogen atom, an alkanoyloxy group, a phenylthio group, a phenoxythio group, a phenoxyoxythio group, a benzoylthio group, a di(alkoxy)phosphono group, a trimethylsilyl group, a di(alkoxy)boryl group, a cycloalkyl group, a heterocyclic group which contains 1 to 4 atoms selected from nitrogen atom, oxygen atom and sulfur atom as a hetero atom(s) (said heterocyclic group may have a substituent(s))or an aryl group which may have a substituent(s), etc. As a substituent for the alkyl group of R, an alkoxycarbonyl group, cyano group or an alkoxyalkyl group is preferably used. More specifically, those in which R is 4-alkoxycarbonylbutyl group, 4-cyanobutyl group, 4-alkoxybutyl group or 3-alkoxybutyl group are preferably used.

As the heterocyclic group which is a substituent for the alkyl group of R, a saturated or unsaturated monocyclic or bicyclic heteroaromatic cyclic group may be mentioned, and there may be mentioned, for example, thienyl group, furyl group, tetrahydrofuryl group, pyranyl group, pyrrolyl group, imidazolyl group, pyrazolyl group, isothiazolyl group, isoxazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, piperazinyl group, morpholinyl group, benzothienyl group, benzofuryl group, isobenzofuranyl group, chromenyl group, indolyl group, isoindolyl group, indazolyl group, purinyl group, quinolizinyl group, naphthidinyl group, quinoxalinyl group, cinnolinyl group, quinolyl group, isoquinolyl group, benzothiazolyl group, benzisothiazolyl group, quinozolinyl group, phthalazinyl group, benzoxazolyl group, benzimidazolyl group, pteridinyl group, pyridopyrimidinyl group, isochromanyl group, chromanyl group, indolinyl group, isoindolinyl group, tetrahydroquinolyl group, tetrahydroisoquinolyl group, tetrahydroquinoxalinyl group, dihydrophthalazinyl group, etc. As a substituent for the heterocyclic group, a dialkylamino group, an alkoxycarbonyl group, an alkyl group or formyl group may be mentioned.

Also, as the aryl group which is a substituent for the alkyl group of R, phenyl group, naphthyl group, anthracenyl group, etc. may be mentioned, and phenyl group is preferably used. As a substituent for the aryl group, an alkoxycarbonyl group, an alkanoyl group, cyano group, an alkanoyloxy group, an alkoxy group, di(trimethylsilyl) amino group, etc. may be mentioned.

As the bicyclo group of R, bicyclo[2.2.1]heptan-7-yl group, bicyclo[4.1.0]heptan-7-yl group, etc. may be mentioned. Also, as a substituent for the bicycle group, an alkanoylamino group, etc. may be mentioned.

As a substituent for the alkenyl group of R, a cycloalkyl group, an aryl group which may have a substituent(s), an alkanoyloxy group, an alkanoyl group, an alkylphenylsulfoxy group, a phenylsulfoxyamino group, a halogenoalkyl group, etc. may be mentioned. As the aryl group, phenyl group, naphthyl group, anthracenyl group, etc. may be mentioned, and phenyl group is preferably used. As a substituent for the aryl group, an alkoxycarbonyl group, etc. may be mentioned.

As a substituent for the aryl group of R, an alkyl group, a halogenoalkyl group, an alkoxycarbonyl group, an alkanoyl group, a dialkylaminocarbonoyl group, cyano group, a halogen atom, etc. may be mentioned. As the aryl group, phenyl group, naphthyl group, anthracenyl group, etc. may be mentioned, and phenyl group is preferably used.

As the heterocyclic group which contains 1 to 4 atoms selected from nitrogen atom, oxygen atom and sulfur atom as a hetero atom(s) of R, a saturated or unsaturated monocyclic or bicyclic heteroaromatic cyclic group may be mentioned, and there may be mentioned, for example, thienyl group, furyl group, tetrahydrofuryl group, a pyranyl group, pyrrolyl group, imidazolyl group, pyrazolyl group, isothiazolyl group, isoxazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, piperazinyl group, morpholinyl group, benzothienyl group, benzofuryl group, isobenzofuranyl group, chromenyl group, indolyl group, isoindolyl group, indazolyl group, purinyl group, quinolizinyl group, naphthidinyl group, quinoxalinyl group, cinnolinyl group, quinolyl group, isoquinolyl group, benzothiazolyl group, benzisothiazolyl group, quinozolinyl group, phthalazinyl group, benzoxazolyl group, benzimidazolyl group, pteridinyl group, pyridopyrimidinyl group, isochromanyl group, chromanyl group, indolinyl group, isoindolinyl group, tetrahydroquinolyl group, tetrahydroisoquinolyl group, tetrahydroquinoxalinyl group, dihydrophthalazinyl group, etc., and of these, pyridyl group, thienyl group, imidazolyl group, thiazol group are preferably used. As a substituent for the heterocyclic group, an alkyl group, an alkoxycarbonyl group, benzoyl group, an alkanoyl group or cyano group, etc. may be mentioned.

Moreover, in the process of the present invention, it is preferred that R is an alkyl group which may have a substituent(s), and as the substituent for the alkyl group, an alkoxycarbonyl group, cyano group or an alkoxy group is preferred. More specifically, R is preferably 4-alkoxycarbonylbutyl group, 4-cyanobutyl group, 4-alkoxycarbonyl group or 3-alkoxybutyl group. As the 4-alkoxycarbonylbutyl group, 4-ethoxycarbonylbutyl group is mentioned.

In particular, in the process of the present invention, the reaction is preferably carried out wherein R is an alkoxycarbonylalkyl group, a cyanoalkyl group or an alkoxyalkyl group, by using zinc in the presence of bromine.

Also, Compound (IX) can be produced by, after suspending zinc or magnesium in a solvent and adding a salt (X), reacting with Compound (VIII). As the solvent, any solvent which does not cause any unfavorable effect to the reaction may be used, and for example, tetrahydrofuran, toluene, diethyl ether, 1,2-dimethoxyethane, acetonitrile, 1,4-dioxane, etc. may be mentioned, and a mixed solvent of these solvents may be used. The present reaction proceeds at −50° C. to 150° C., particularly preferably at 5° C. to 80° C. As a metal atom (M) of the salt (X), a typical metal or a transition metal, etc. may be mentioned. As the typical metal, lithium, sodium, potassium, cesium, magnesium, calcium, barium, aluminum, zinc, silicon, tin, etc. may be mentioned, and as the transition element, titanium, chromium, molybdenum, tungsten, manganese, iron, ruthenium, cobalt, rhodium, nickel, palladium, platinum, copper, etc. may be mentioned.

As a salt of the compounds represented by Compound (I), Compound (I-a), Compound (I-b), Compound (II), Compound (II'), Compound (II-a), Compound (II-b), Compound (II-c), Compound (III), Compound (III-a), Compound (IV), Compound (IV-a), Compound (VI), Compound (6) or Compound (6-a) which is obtained or obtainable in the present invention, there may be mentioned, for example, inorganic salts (hydrochloride, phosphate, hydrobromide, sulfate, etc.) or a salt with an organic acid (acetate, formate, propionate, fumarate, maleate, succinate, tartarate, citrate, malate, oxalate, benzoate, methanesulfonate, benzenesulfonate, tosylate, etc.). Moreover, when the compound of the present invention has an acidic group such as a carboxylic acid, the compound of the present invention may form a salt with, for example, an inorganic base (an alkali metal salt such as sodium salt, potassium salt, etc., an alkaline earth metal salt such as calcium salt, magnesium salt, etc., ammonium salt, etc.) or an organic base (an amino acid salt such as triethylamine salt, lysine salt, etc.). A free compound and a salt can be mutually converted into the other by a conventionally known method or a method in accordance with the method.

In the present specification, as the alkyl group or the alkoxy group, straight or branched one having 1 to 6 carbon atoms, particularly straight or branched one having 1 to 4 carbon atoms may be mentioned. As the alkanoyl group, the alkoxycarbonyl group or the alkylthiocarbonyl group, straight or branched one having 2 to 7 carbon atoms, particularly straight or branched one having 2 to 5 carbon atoms may be mentioned. As the halogen atom, fluorine atom, chlorine atom, bromine atom or iodine atom may be mentioned. As the halogenoalkyl group, trifluoromethyl group, etc. may be mentioned.

EXAMPLE

Next, the present invention will be explained by referring to Examples, but the present invention is not limited only by such Examples.

Example 1

(1) In 45 ml of dimethylsulfoxide was dissolved 20 g of (4R)-3-benzyl-4-hydroxymethylthiazolidin-2-one under room temperature, 1.45 ml of pyridine, 1.38 ml of trifluoroacetic acid, and 30 ml of ethyl acetate were added to the solution in this order. At 25° C., 22.2 g of dicyclohexylcarbodiimide and 15 ml of ethyl acetate were added to the above mixture, and the resulting mixture was stirred at 50° C. for 3 hours. To the reaction mixture was added 100 ml of ethyl acetate, the mixture was stirred at 10° C. or lower for 30 minutes, and precipitated product was filtered off. The filtrate was washed with brine (saturated brine:water=1:1), and the aqueous layer was further extracted with ethyl acetate. The organic layers were combined, washed with brine (saturated brine:water=1:1), dried, and concentrated to obtain (4R)-2-oxo-3-benzylthiazolidin-4-carbaldehyde.

(2) The compound obtained in Example 1-(1) was dissolved in 50 ml of dichloromethane, and at 20° C. to 25° C., 5 g of magnesium sulfate was added to the solution. At 5° C. or lower, 4.89 ml of benzylamine was added to the solution, and the resulting mixture was stirred at 20° C. to 25° C. for 1.5 hours. After cooling the solution to –5° C., 15 ml of an aqueous solution containing 4.39 g of sodium cyanide and 5.1 ml of acetic acid was added to the mixture at –5° C. to 0° C. Then, after a temperature of the solution was raised to 20° C. to 25° C. over 4 hours, it was stirred for 12 hours. To the solution was added 50 ml of dichloromethane, and the mixture was washed with a saturated aqueous sodium hydrogen carbonate solution and water. The organic layer was dried and concentrated to give 13.47 g of a mixture of a syn isomer and an anti isomer of (4R)-4-[1-(N-benzylamino)-1-cyanomethyl]-3-benzylthiazolidin-2-one as pale yellowish crystals. When optical purity of the mixture was analyzed by high performance liquid chromatography (HPLC), it had a ratio of syn isomer:anti isomer=14:1.

(HPLC Conditions)

Column: L-column ODS (4.6×150 mm) [manufactured by Shimadzu Corporation], mobile layer: 0.01M $KH_2PO_4$ (pH=3)/acetonitrile=50/50, flow rate: 0.5 ml/min, UV detection: 225 nm, column temperature: 40° C.

syn isomer: Melting point: 124-125° C. $[\alpha]_D^{25}$: +46.1° (C=1.0, chloroform) Optical purity (HPLC): 99% ee (HPLC Conditions)

Column: Chiral cell AD-H (4.6×250 mm) [manufactured by Daicel Chemical Industries, Ltd.], mobile layer: ethanol/n-hexane=10/90, flow rate: 0.8 ml/min, UV detection: 225 nm, column temperature: 40° C.

anti isomer: MS.APCI (m/z): 338 [(M+H)$^+$].

(3) The compound obtained in Example 1-(2) was suspended in 30 ml of toluene, and under ice-cooling, 1.44 ml of water and 14.8 ml of conc. sulfuric acid were added to the suspension, and the mixture was stirred at 40° C. for 24 hours. At 30° C. or lower, 7 ml of water, 39 ml of acetone, and 45 ml of water were added to the solution in this order. Then, at 40° C. or lower, 45 ml of conc. aqueous ammonia was added to the solution, and the mixture was stirred at 25° C. for 30 minutes. Precipitated crystal was collected by filtration, washed with acetone, water, and acetone in this order, and dried to give 12.6 g of (4R)-4-[(1R)-1-(N-benzylamino)-1-carbamoylmethyl]-3-benzylthiazolidin-2-one as pale yellowish crystal.

Melting point: 194-195° C. ESI.MS (m/z): 356 (M$^+$+1) $[\alpha]_D^{20}$: –38.8° (C=0.45, N,N-dimethylformamide).

Example 2

In 200 ml of N,N-dimethylformamide was dissolved 100 g of (4R)-4-[(1R)-1-(N-benzylamino)-1-carbamoylmethyl]-3-benzylthiazolidin-2-one, and under nitrogen atmosphere, the solution was stirred at 85° C. for 5 hours. At 90° C. to 95° C., 200 ml of 35% hydrochloric acid was added dropwise to the solution, and the mixture was stirred for 1 hour and 15 minutes. Moreover, 100 ml of 35% hydrochloric acid was added dropwise, and the mixture was stirred for 2 hours. Then, 200 ml of water was added dropwise to the mixture at 85° C. The solution was ice-cooled, and precipitated crystal was collected by filtration, washed with water and then dried at 50° C. for 17 hours to give 93.1 g of (4R,5R)-1,3-dibenzyl-2-oxo-5-(mercaptomethyl)-imidazolidin-4-carboxylic acid as colorless crystal.

Melting point: 159-160° C. ESI.MS (m/z): 357 (M$^+$+1) $[\alpha]_D^{20}$: +48.8° (C=0.62, N,N-dimethylformamide).

Example 3

To 240 ml of a chloroform solution containing 30 g of (4R,5R)-1,3-dibenzyl-2-oxo-5-(mercaptomethyl)imidazolidin-4-carboxylic acid, 22.7 g of pyridine and 2.6 ml of trifluoroacetic acid was added dropwise 60 ml of a chloroform solution containing 17.4 g of dicyclohexylcarbodiimide at 5° C. over 30 minutes. After the solution was refluxed for 5 hours, it was concentrated under reduced pressure. The concentrate was dissolved in ethyl acetate and concentrated, and after the procedure was repeated, 300 ml of ethyl acetate was added to the residue, and the mixture was stirred at 50° C. for 30 minutes. After cooling to 25° C., insoluble materials were filtered off. After the filtrate was concentrated, 85 ml of methanol was added to the concentrate and the mixture was dissolved under heating. After cooling the solution, precipitated crystal was collected by filtration, and washed with cold methanol. Precipitated crystal was dried by blowing air at 50° C. to give 21.3 g of (3aS,6aR)-1,3-dibenzyl-hexahydro-4H-thieno[3,4-d]imidazol-2,4-dione as colorless crystal.

Melting point: 122-123° C. $[\alpha]_D^{25}$: +90.5° (C=1.0, chloroform).

Example 4

Under nitrogen atmosphere, 30.4 g of zinc powder was suspended in 55 ml of tetrahydrofuran, 3.5 ml of trimethylsilyl chloride was added to the suspension, and the mixture was stirred for 15 minutes. After heating to 40° C., dropwise addition of 102.9 g of ethyl 5-iodovalerate to the mixture was started. Whereas exothermic reaction occurs simultaneously with starting the dropwise addition, the dropwise addition was continued so that the mixture was maintained at 60° C. to 65° C. After completion of dropwise addition, the mixture was washed with 5 ml of tetrahydrofuran, immersed in an outer bath at 55° C. while continuing stirring (total time of the dropwise addition and stirring: 50 minutes), and after disappearance of ethyl 5-iodovalerate was confirmed by high performance liquid chromatography, the mixture was cooled to 23° C. To the mixture were added 125 ml of toluene, 52.5 g of (3aS,6aR)-1,3-dibenzyl-hexahydro-4H-thieno[3,4-d]imidazol-2,4-dione, 1.09 g of 10% palladium hydroxide on carbon, 50 ml of toluene, and 11.5 ml of N,N-dimethylformamide in this order, and the resulting mixture was stirred at 24° C. to 35.5° C. for 50 minutes. The reaction mixture was filtered by using 12 g of activated charcoal and 32.5 g of Celite, and washed with 200 ml of tetrahydrofuran. The filtrate and the washing solution were combined, and after washing with 2M hydrochloric acid, it was washed with water and concentrated. The concentrated residue was dissolved in 390 ml of toluene, 2.95 g of p-toluenesulfonic acid.monohydrate was added to the solution, and the mixture was stirred at 20° C. to 25° C. for 1.5 hours. At 40° C. to 45° C., about 100 ml of the solvent was distilled off, and the reminder was successively washed with water, sodium thiosulfate aqueous solution and water in this order, and further concentrated to give 60.6 g of ethyl (5Z)-5-[(3aS,6aR)-1,3-dibenzyl-hexahydro-2-oxo-4H-thieno-[3,4-d]imidazol-4-yliden]pentanoate as oily product.

Example 5

400 ml of purified water, 12.85 g of 20% palladium hydroxide on carbon (50% wet), 900 ml of a methanol solution containing 249.5 g of ethyl (5Z)-5-[(3aS,6aR)-1,3-dibenzyl-hexahydro-2-oxo-4H-thieno[3,4-d]imidazol-4-yliden]pentanoate were added successively in this order, and the atmosphere was replaced with 490 kPa hydrogen three times. Moreover, 627 kPa hydrogen pressure was applied at 6.5° C., and the mixture was stirred at 500 rpm. The reaction temperature and the pressure became 92.5° C. and 843 kPa at 50 minutes after initiation of heating, 117° C. and 921 kPa after 4 hours, and 116° C. and 853 kPa after 11 hours, so that hydrogen was charged up to 882 kPa. After 24 hours, the reaction mixture was cooled at 115° C. and 892 kPa, washed with methanol, and the catalyst was filtered off. The filtrate was concentrated, 400 ml of toluene was added to the residue, and replacement and concentration were carried out three times with an outer bath at 65° C. To the above-mentioned residue were added 1206 ml of methanol, 402 ml of water and 53.3 g of sodium hydroxide, the resulting mixture was stirred at 40° C. for 2 hours. To the reaction mixture was added 300 g of 10% aqueous hydrochloric acid, the mixture was neutralized to pH 7, 6 g of activated charcoal was added to the mixture and the resulting mixture was stirred at room temperature for 40 minutes. The reaction mixture was subjected to precoat filtration with 6 g of activated charcoal. Methanol was distilled of under reduced pressure, and 600 ml of ethyl acetate was added. 10% aqueous hydrochloric acid was added to the mixture to carry out extraction (pH of the aqueous layer was 0.7), and the organic layer was washed with 10% brine. The organic layer was dried over anhydrous magnesium sulfate, and filtered. The filtrate was concentrated under reduced pressure, and when no ethyl acetate was distilled off, the residue was subjected to replacement with 170 ml of mesitylene and concentration two times to give 170.1 g of (3aS,4S,6aR)-1, 3-dibenzyl-hexahydro-2-oxo-4H-thieno[3,4-d]imidazol-4-pentanoic acid as colorless oily product.

Example 6

A mixture of 3.0 g of (3aS,4S,6aR)-1,3-dibenzyl-hexahydro-2-oxo-4H-thieno[3,4-d]imidazol-4-pentanoic acid and 24 ml of 48% hydrobromic acid was refluxed at 110° C. to 120° C. for 48 hours. Hot extraction with 10 ml of toluene was carried out four times to remove benzyl bromide. The aqueous layer was concentrated, 15 ml of water and 11.5 ml of 6M aqueous sodium hydroxide solution were added to the residue, subsequently 3.36 g of ethoxycarbonyl chloride was added dropwise, and the reaction was carried out while maintaining pH to 8 to 10, at room temperature for 3 hours. Thereafter, a temperature of the reaction mixture was raised to 70° C. to 80° C., and the reaction was carried out for 20 hours (during the reaction, pH was maintained to 12 by adding 6M aqueous sodium hydroxide solution). pH was adjusted to 7.4 to 7.8 with 7 ml of 16% hydrochloric acid, and filtration was carried out at 90° C. to 95° C. by using 1.0 g of activated charcoal. The filtrate was heated to 80° C. to 85° C., pH thereof was adjusted to 1.8 to 2.2 by using 6 ml of 16% hydrochloric acid, and neutralization crystallization was carried out. After cooling, crystal was collected by filtration and washed with water, and dried by blowing air at 50° C. to give 1.38 g of (+)-biotin as colorless crystal.

Example 7

(1) 79.3 g of (4R)-3-benzyl-4-hydroxymethylthiazolidin-2-one was treated in the same manner as in Example 1-(2), and after the precipitated crystal was filtered off, the filtrate was concentrated. The residue was purified by silica gel chromatography (hexane:chloroform:ethyl acetate=5:5:1) to give 9.3 g of (4R)-4-[(1S)-1-(N-benzylamino)-1-cyanomethyl]-3-benzylthiazolidin-2-one.
Melting point: 131-132° C. $[\alpha]_D^{23}$: −174.7° (C=1.0, chloroform) MS.APCI (m/z): 338 [(M+H)$^+$].
(2) 6.0 g of (4R)-4-[(1S)-1-(N-benzylamino)-1-cyanomethyl]-3-benzylthiazolidin-2-one was treated in the same manner as in Example 1-(3) to give (4R)-4-[(1S)-1-(N-benzylamino)-1-carbamoylmethyl]-3-benzylthiazolidin-2-one as colorless oily product. Then, it was dissolved in ethyl acetate, 6 ml of 4M hydrogen chloride-ethyl acetate solution was added, and precipitated crystal was collected by filtration to give 4.3 g of (4R)-4-[(1S)-1-(N-benzylamino)-1-carbamoylmethyl]-3-benzylthiazolidin-2-one hydrochloride.
ESI.MS (m/z): 356 (M$^+$+1) $[\alpha]_D^{23}$: −32.6° (C=1.0, methanol).
(3) In 10 ml of N,N-dimethylformamide was dissolved 0.541 g of (4R)-4-[(1S)-1-(N-benzylamino)-1-carbamoylmethyl]-3-benzylthiazolidin-2-one hydrochloride, the solution was stirred under nitrogen atmosphere at 100° C. for 3 hours. Ethyl acetate was added to the reaction mixture, and the resulting mixture was washed with water, and saturated brine, dried and concentrated. The residue was crystallized from hexane to give 342 mg of (3aS,6aR)-1,3-dibenzyl-hexahydro-4H-thieno[3,4-d]imidazol-2,4-dione as colorless crystal.
Optical purity (HPLC): >91% ee (HPLC Conditions)
Column: Chiral cell AD (4.6×250 mm) [manufactured by Daicel Chemical Industries, Ltd.], mobile layer: ethanol/hexane=15/85, flow rate: 0.8 ml/min, UV detection: 225 nm, column temperature: 40° C.

Example 8

In 160 ml of chloroform was dissolved 20 g of (4R,5R)-1,3-dibenzyl-2-oxo-5-(mercaptomethyl)imidazolidin-4-carboxylic acid, 6.2 g of pyridine was added to the solution, and under ice-cooling, 40 ml of a chloroform solution containing 12.7 g of dicyclohexylcarbodiimide was added to the mixture at 15° C. or lower. The mixture was stirred at room temperature for 1 hour, ethyl acetate was added to the reaction mixture and the resulting mixture was filtered. The filtrate was washed successively with 2M hydrochloric acid, water, a saturated sodium bicarbonate solution, and saturated brine. The organic layer was dried and then concentrated. The residue was recrystallized from ethyl acetate to give 8.0 g of (3aR,6aR)-1,3-dibenzyl-hexahydro-4H-thieno [3,4-d]imidazol-2,4-dione.
Melting point: 115-116° C. $[\alpha]_D^{26}$: +10.6° (C=1.0, chloroform).

Example 9

In 1 ml of chloroform was dissolved 100 mg of (3aR,6aR)-1,3-dibenzyl-hexahydro-4H-thieno[3,4-d]imidazol-2,4-dione, 0.5 ml of pyridine was added to the solution, and the resulting mixture was stirred at room temperature for 23 hours. The reaction mixture was successively washed with 2M hydrochloric acid, water, a saturated sodium bicarbonate solution, and saturated brine. The organic layer was dried and then concentrated. By adding isopropyl ether, precipitated crystal was collected by filtration to give 75.1 mg of (3aS,6aR)-1,3-dibenzyl-hexahydro-4H-thieno[3,4-d]imidazol-2,4-dione.
Melting point: 122-123° C. $[\alpha]_D^{25}$: +90.5° (C=1.0, chloroform).

Example 10

To 39 ml of an N,N-dimethylformamide solution containing 14 g of (4R)-4-[(1R)-1-(N-benzylamino)-1-carbamoylmethyl]-3-benzylthiazolidin-2-one was added 3.96 g of sodium bicarbonate, and the mixture was stirred at 80 to 85° C. for 17 hours. The reaction mixture was concentrated under reduced pressure, 40 ml of methanol and 20 ml of water were added to the concentrated residue and the resulting mixture was stirred at 5° C. or lower for 1 hour. Precipitated crystal was collected by filtration, washed with a mixed solution comprising 80 ml of methanol and 40 ml of water, and then, dried by blowing air at 50° C. for 17 hours to give 12.14 g of (4S,4'S,5R,5'R)-5,5'-[dithiobis (methylene)]bis(1,3-dibenzyl-2-oxoimidazolidin-4-carboxamide) as pale yellowish crystal.

Melting point: 208-211° C. ESI.MS (m/z): 709 (M$^+$+1) $[\alpha]_D^{20}$: +55.4° (C=0.29, N,N-dimethylformamide).

Example 11

In 5 ml of acetic acid was dissolved 497 mg of (4S,4'S, 5R,5'R)-5,5'-[dithiobis(methylene)]bis(1,3-dibenzyl-2-oxoimidazolidin-4-carboxamide), 249 mg of zinc powder was added to the solution, and the resulting mixture was stirred at 90° C. for 1.5 hours. Ethyl acetate was added to the reaction mixture and the mixture was filtered by adding Celite. After the filtrate was concentrated under reduced pressure, ether and hexane were added to the residue. Precipitated crystal was collected by filtration, washed with water and hexane, and then, dried under reduced pressure to give 482 mg of (4R,5R)-1,3-dibenzyl-2-oxo-5-(mercaptomethyl)imidazolidin-4-carboxamide as colorless crystal.

Melting point: 119-122° C. ESI.MS (m/z): 356 (M$^+$+1) $[\alpha]_D^{20}$: −1.2° (C=0.33, N,N-dimethylformamide).

Example 12

In 24 ml of acetic acid was dissolved 12 g of the compound obtained in Example 10, 7.2 g of zinc powder was added to the solution, and the resulting mixture was stirred at 55 to 60° C. for 1 hour. After the reaction mixture was cooled to 20° C., 72 ml of conc. hydrochloric acid was added to the mixture and the resulting mixture was stirred at 80 to 90° C. for 2 hours. To the reaction mixture was added 120 ml of water, and after cooling to 25° C. over 1 hour, the mixture was stirred at 5° C. or lower for 1 hour. Precipitated crystal was collected by filtration, washed with 95 ml of water and dried under reduced pressure to give 11.05 g of (4R,5R)-1,3-dibenzyl-2-oxo-5-(mercaptomethyl)imidazolidin-4-carboxylic acid as colorless crystal.

Physical properties of this product accorded to those of Example 2.

Example 13

In 210 ml of dimethylsulfoxide was dissolved 23.5 g of (4R)-4-[(1R)-1-(N-benzylamino)-1-cyanomethyl]-3-benzylthiazolin-2-one, 1.35 g of potassium carbonate (fine powder) was added to the solution, and further 12 ml of 30% aqueous hydrogen peroxide was added dropwise at 20° C. to 25° C., and then, the resulting mixture was stirred at room temperature for 1 hour. To the liquid was further added 12 ml of 30% aqueous hydrogen peroxide, and after stirring at 20° C. for 13 hours, 210 ml of water was added thereto at room temperature and the mixture was stirred for 3 hours. Precipitated crystal was collected by filtration, washed with water and acetone, and then, dried by blowing air at 50° C. overnight to give 21.8 g of (4R)-4-[(1R)-1-(N-benzylamino)-1-carbamoylmethyl]-3-benzylthiazolin-2-one as colorless powder. Physical properties of this product accorded to those of Example 1-(3).

Example 14

(1) In a mixed solution comprising 180 ml of tetrahydrofuran and 120 ml of toluene was suspended 92.8 g of zinc powder, 58 g of bromine was added at 10° C. to 37° C. over 15 minutes, and then, a temperature of the liquid was raised to 50° C. over 15 minutes. To the solution was added dropwise 186.4 g of ethyl 5-iodovalerate at 50° C. to 55° C. for 3.5 hours.

(2) After cooling the solution obtained in Example 14-(1) to 30° C., 360 ml of toluene, 176 g of (3aS,6aR)-1,3-dibenzyl-hexahydro-4H-thieno[3,4-d]imidazol-2,4-dione and 44 ml of an N,N-dimethylformamide suspension containing 4.8 g of palladium catalyst (manufactured by Degussa Corporation; E 1002 NN/D 10% Pd) were successively added to the solution, and the resulting mixture was stirred at 28° C. to 40° C. for 17 hours. To the solution was added hydrochloric acid (157 ml of conc. hydrochloric acid+184 ml of water) at 10° C. to 30° C., and the mixture was stirred at 20° C. for 1 hour. After filtration of the solution, a temperature of the filtrate was raised to 40° C. over 40 minutes, and the solution was separated. The organic layer was washed successively with water, an aqueous sodium hydrogen carbonate solution, an aqueous sodium sulfite solution, and water in this order, and concentrated. Toluene was added to the residue, and the mixture was further concentrated. The residue was dissolved in 67 ml of methanol, and 6.7 g of activated charcoal was added to the solution and the mixture was filtered. The residue was washed with 67 ml of methanol, and combined with the filtrate to use the next step.

The product obtained by the above-mentioned reaction was partially saponified to make (5Z)-5-[(3aS,6aR)-1,3-dibenzyl-hexahydro-2-oxo-4H-thieno[3,4-d]imidazol-4-yliden]pentanoic acid and an amount thereof was quantitated by HPLC under the following conditions whereby it had been confirmed that 220 g of ethyl (5Z)-5-[(3aS,6aR)-1,3-dibenzyl-hexahydro-2-oxo-4H-thieno[3,4-d]imidazol-4-yliden]pentanoate was obtained by the above-mentioned reaction.

(HPLC Conditions)
Column: L-column ODS (4.6×150 mm) (manufactured by Shimadzu Corporation), mobile layer: acetonitrile/potassium hydrogen diphosphate (pH 3)=40/60, flow rate: 1.0 ml/min, UV detection: 254 nm, column temperature: 40° C.

(3) To 88 ml of a methanol solution obtained in Example 14-(2) were added 313 ml of methanol, 110 ml of water and 9.06 g of palladium catalyst (manufactured by Degussa Corporation; E 106 NN/W 5% Pd), and the mixture was stirred under a hydrogen pressure of 9 khPa at an inner temperature of 110° C. for 16 hours. After cooling the solution, the catalyst was filtered off, and the filtrate was washed with 350 ml of methanol. To the filtrate was added an aqueous sodium hydroxide solution (14.6 g of sodium hydroxide+55 ml of water), and the mixture was stirred at 50° C. for 1 hour. To the solution was added 10% hydrochloric acid at 30° C. or lower until the solution became pH 7, then the solution was concentrated. To the residue was added toluene, and the mixture was further concentrated. After the residue was dissolved in 300 ml of toluene, at 40° C. under heating, the mixture was washed with 10% hydrochloric acid and water. The organic layer was quantitated by HPLC under the following conditions to confirm that 52 g of (3aS,4S,6aR)-1,3-dibenzyl-hexahydro-2-oxo-4H-thieno[3,4-d]imidazol-4-pentanoic acid obtained in the above-mentioned reaction was obtained.

(HPLC Conditions)

Column: L-column ODS (4.6×150 mm) (manufactured by Shimadzu), mobile layer: acetonitrile/potassium hydrogen diphosphate (pH 3)=40/60, flow rate: 1.0 ml/min, UV detection: 254 nm, column temperature: 40° C.

(4) After the toluene solution obtained in Example 14-(3) was concentrated, mesitylene was added thereto and concentrated. The residue was dissolved in 166 ml of mesitylene, 108 ml of methanesulfonic acid was added to the solution, and the mixture was stirred at 133° C. for 1 hour. The solution was cooled up to 80° C., 15 ml of acetic acid was added to the solution, and the solution was added dropwise to 1040 ml of purified water at 30° C. or lower. After the solution was ice-cooled for 1 hour, precipitated crystal was collected by filtration, washed with water and acetone, and dried under reduced pressure to give 25.7 g of crude biotin.

In an aqueous sodium hydroxide solution (4.42 g of sodium hydroxide+330 ml of water) was dissolved 24.6 g of crude biotin, and a pH thereof was adjusted to 8.5 at 50° C. to 60° C. by using dil. hydrochloric acid. To the solution was added 16 g of activated charcoal at 50° C. to 60° C., and after the mixture was stirred for 10 minutes, and then, filtered. The filtrate was heated to 90° C. to 95° C., and a pH of the solution was adjusted to 1.8-2.2 with conc. hydrochloric acid, and then, neutralization crystallization were carried out. The mixture was stirred at the same temperature for 30 minutes to grow crystal. The solution was gradually cooled, and after ice-cooling, precipitated crystal was collected by filtration. The crystal was subjected to drying by blowing air at 50° C. overnight to give 22.4 g of (+)-biotin.

Reference Example 1

(1) A aqueous solution comprising 0.88 liter of water and 184.0 g of sodium hydroxide was dissolved 175.6 g of L-cysteine monohydrochloride monohydrate under ice-cooling, 0.35 liter of a toluene solution containing 313.2 g of phenyl chloroformate was added to the above solution within a range not exceeding 30° C. After stirring the mixture at room temperature for 2 hours, it was allowed to stand and the liquids were separated. The aqueous layer was washed with 0.35 liter of toluene, the layers were separated, and the aqueous layer was concentrated to give 139.84 g of (4R)-2-oxothiazolidin-4-carboxylic acid as colorless crystal.

Melting point: 168-170° C. MS.APCI (m/z): 148 [(M+H)$^+$] [α]$_D^{25}$: −62.8° (C=1.0, H$_2$O).

(2) To 1.47 g of the compound obtained in Reference Example 1-(1) were successively added an aqueous solution comprising 1.5 ml of water and an aqueous solution containing 0.6 g of sodium hydroxide and 4.4 ml of dimethylsulfoxide under ice-cooling. To the mixture was added 2.3 ml of benzyl chloride at room temperature, and the resulting mixture was stirred for 15 hours. The mixture was neutralized by dil. hydrochloric acid, and extracted with ethyl acetate. The organic layer was washed with water and saturated brine, dried over anhydrous magnesium sulfate, and then, insoluble material was filtered off and the filtrate was concentrated to give 2.24 g of (4R)-2-oxo-3-benzylthiazolidin-4-carboxylic acid as colorless crystal.

Melting point: 95-97° C. MS.APCI (m/z): 238 [(M+H)$^+$] [α]$_D^{25}$: −102.2° (C=1.0, chloroform).

(3) To 32 ml of tetrahydrofuran was added 1.53 g of sodium borohydride under room temperature, and the mixture was cooled to 10° C. To the mixture was added 8.0 g of the compound obtained in Reference Example 1-(2), and further 2 ml of a tetrahydrofuran solution containing 2.0 g of sulfuric acid was added to the mixture. The mixture was stirred at 40° C. to 50° C. for 3 hours, the reaction mixture was ice-cooled and 2M hydrochloric acid was added to the mixture until a pH of the mixture became 1. The reaction mixture was diluted with ethyl acetate, and the layers were separated. The organic layer was washed with water, dried over anhydrous magnesium sulfate, and then concentrated under reduced pressure. The residue was recrystallized from diisopropyl ether to give 6.82 g of (4R)-3-benzyl-4-hydroxymethylthiazolidin-2-one as colorless crystal.

Melting point: 87-90° C. MS.APCI (m/z): 224 [(M+H)$^+$] [α]$_D^{25}$: −26.7° (C=1.0, methanol) Optical purity (HPLC): >99% ee (HPLC Conditions)

Column: Chiral cell AD (4.6×250 mm) [manufactured by Daicel Chemical Industries, Ltd.], mobile layer: ethanol/hexane=10/90, flow rate: 0.8 ml/min, UV detection: 225 nm, column temperature: 40° C.

(4) In 5.0 ml of dimethylsulfoxide was dissolved 1.0 g of the compound obtained in Reference Example 1-(3), and 1.95 ml of diisopropylethylamine was added dropwise thereto under room temperature. The reaction mixture was ice-cooled, and then, 1.78 g of sulfur trioxide pyridine complex salt was added thereto at 12° C. to 20° C., and the resulting mixture was stirred at the same temperature for 30 minutes. The reaction mixture was poured into 30 ml of ice-cold water, and extracted with 20 ml of ethyl acetate. The aqueous layer was extracted again with 10 ml of ethyl acetate. The ethyl acetate layers were combined, washed twice with 10 ml of 10% citric acid, and then, washed with 10 ml of water and 10 ml of saturated brine, respectively. The extract was dried over anhydrous magnesium sulfate, and concentrated under reduced pressure to give 985.9 mg of (4R)-2-oxo-3-benzylthiazolidin-4-carbaldehyde as colorless oily product.

MS.APCI (m/z): 222 [(M+H)$^+$].

Reference Example 2

In 22 ml of dichloromethane was dissolved 2.34 g of dimethylsulfoxide, and 1.31 ml of oxalyl chloride was added thereto at −78° C. After stirring the mixture at the same temperature for 10 minutes, 11 ml of a dichloromethane solution containing 2.23 g of the compound obtained in Reference Example 1-(3) was added dropwise to the mixture at −60° C. or lower. After stirring the mixture at −78° C. for 20 minutes, 5.58 ml of triethylamine was added dropwise at −60° C. or lower. A reaction temperature of the mixture was raised to −20° C. over 1.5 hours, and then, the reaction mixture was added to 10% aqueous citric acid, and the layers were separated. The organic layer was washed with saturated brine, dried over anhydrous magnesium sulfate, and concentrated under reduced pressure to give 2.20 g of the same objective compound as in Reference Example 1-(4). Physical properties of this product accorded to those of Reference Example 1-(4).

Reference Example 3

In 11 ml of dichloromethane was dissolved 532 mg of chlorine, and 0.73 ml of dimethylsulfide was added thereto at −20° C. to −10° C. After stirring the mixture at the same temperature for 10 minutes, 5.5 ml of a dichloromethane solution containing 1.12 g of the compound obtained in Reference Example 1-(3) was added dropwise thereto at −25° C. After stirring the mixture at −25° C. for 20 minutes, 2.79 ml of triethylamine was added dropwise thereto at −25 to −18° C. After stirring the mixture at −25° C. for 10 minutes, the reaction mixture was added to 10% aqueous citric acid, and the layers were separated. The organic layer was washed with saturated brine, dried over anhydrous magnesium sulfate, and concentrated under reduced pressure to give 1.17 g of the same objective compound as in Reference Example 1-(4). Physical properties of this product accorded to those of Reference Example 1-(4).

Reference Example 4

In a mixed solvent comprising 6 ml of dichloromethane and 1 ml of water were dissolved 447 mg of the compound obtained in Reference Example 1-(3), 6.9 mg of 4-hydroxytetramethylpiperidineoxide and 206 mg of sodium bromide, and a mixture comprising 1.49 g of aqueous sodium hypochlorite, 491 mg of sodium bicarbonate and 5 ml of water was gradually added dropwise to the solution while effecting nitrogen bubbling and under ice-cooling. After stirring the mixture for one hour, the layers were separated, and the organic layer was washed with 16 mg of potassium iodide, a 10% aqueous potassium hydrogen sulfate solution and an aqueous sodium thiosulfate solution, respectively. The organic layer was dried over anhydrous magnesium sulfate, and concentrated under reduced pressure to give 147.5 mg of the same objective compound as in Reference Example 1-(4). Physical properties of this product accorded to those of Reference Example 1-(4).

Reference Example 5

(1) To the solution comprising 2 liters of water containing 180 g of sodium hydroxide was dissolved 175.6 g of L-cysteine monohydrochloride monohydrate under ice-cooling and under nitrogen atmosphere. To the solution was added dropwise 700 ml of a 1,4-dioxane solution containing 118.7 g of triphosgene at 25° C. to 29° C. over 1 hour and 30 minutes, and further stirred at the same temperature for 3 hours. To the reaction mixture was added conc. hydrochloric acid to adjust the mixture to weak acidic solution, and then, the solvent was removed under reduced pressure. To the concentrated residue was added 200 ml of toluene, and the solvent was removed again under reduced pressure. To the concentrated residue was added 700 ml of ethanol, 131 g of thionyl chloride was added to the mixture under ice-cooling over 40 minutes, and the resulting mixture was stirred for 19 hours while raising the temperature to room temperature. The solvent was removed under reduced pressure, and then, the concentrated residue was dissolved in 1 liter of ethyl acetate, and the mixture was successively washed with 700 ml of water, 300 ml of an aqueous saturated sodium bicarbonate solution and 500 ml of saturated brine. After the mixture was dried over anhydrous magnesium sulfate, and the solvent was removed under reduced pressure to give 162 g of ethyl (4R)-2-oxothiazolidin-4-carboxylate as oily product.

MS.APCI (m/z): 176 [(M+H)$^+$] [α]$_D^{25}$: −52.7° (C=1.0, chloroform).

(2) 1.79 g of sodium bromide, 5 ml of N,N-dimethylacetamide and 1 ml of benzyl chloride were stirred at 23° C. to 26° C. for 15 hours to give benzyl bromide. Into the solution were added 1.27 g of the compound obtained in Reference Example 5-(1), 2 ml of N,N-dimethylacetamide and 1.1 g of potassium carbonate, and the mixture was reacted at 23° C. to 30° C. for 93 hours. Then, ethyl acetate and 10% aqueous citric acid were added to the mixture, and the aqueous layer was separated. The organic layer was washed with water, dried over anhydrous magnesium sulfate, and then concentrated to give 2.29 g of the residue. The residue was purified by silica gel column chromatography (solvent: n-hexane:ethyl acetate=5:1) to give 1.67 g of ethyl (4R)-2-oxo-3-benzylthiazolidin-4-carboxylate as colorless oily product.

MS.APCI (m/z): 266 [(M+H)$^+$] [α]$_D^{24}$: −96.6° (C=1.0, chloroform) Optical purity (HPLC): 98.1% ee (HPLC Conditions)

Column: Chiral cell OD (4.6×250 mm) [manufactured by Daicel Chemical Industries, Ltd.], mobile layer: ethanol/hexane=5/95, flow rate: 0.8 ml/min, UV detection: 225 nm, column temperature: 40° C.

Reference Example 6

In 227 ml of ethanol was dissolved 28.4 g of ethyl (4R)-2-oxo-3-benzylthiazolidin-4-carboxylate, 2.26 g of sodium borohydride was added to the solution, and the resulting mixture was stirred at room temperature for 15 hours. Moreover, 0.76 g of sodium borohydride was additionally added to the mixture, and the resulting mixture was stirred at room temperature for 2 hours. To the mixture was added conc. hydrochloric acid to neutralize the mixture to be a pH of 6 to 7, and the solution was concentrated. The concentrated residue was dissolved in ethyl acetate, washed three times with water, and the aqueous layer was reverse extracted once with ethyl acetate. The ethyl acetate layers were combined, dried over anhydrous magnesium sulfate, and then, concentrated to give 22.6 g of an oily residue. Isopropyl ether was added to the residue to crystallize the compound, and further the crystal was collected by filtration, washed with isopropyl ether, and dried under reduced pressure to give 18.4 g of (4R)-3-benzyl-4-hydroxymethylthiazolidin-2-one as colorless crystal. Physical properties of this product accorded to those of Reference Example 1-(3).

Reference Example 7

(1) In 200 ml of acetonitrile was dissolved 10 g of (4R)-2-oxo-3-benzylthiazolidin-4-carboxylic acid, and 9.2 g of dicyclohexylcarbodiimide was added to the solution under room temperature. Subsequently, to the solution were added 3.3 ml of ethanethiol, and 670 mg of 4-dimethylaminopyridine in this order under ice-cooling, and the mixture was stirred at room temperature for 2 hours. Insoluble material was filtered off, and the filtrate was concentrated under reduced pressure. The residue was purified by silica gel column chromatography (solvent: n-hexane:ethyl acetate=10:1) to give 10.8 g of (4S)-4-ethylthiocarbonyl-3-benzylthiazolidin-2-one as oily product.

MS.APCI (m/z): 282 [(M+H)$^+$] [α]$_D^{25}$: −110.8° (C=1.04, chloroform).

(2) In 5.0 ml of dichloromethane was dissolved 0.5 g of the compound obtained in Reference Example 7-(1), and 284 mg of palladium hydroxide was added to the solution under nitrogen atmosphere. At room temperature, 0.85 ml of trimethylsilane was added to the mixture, and the resulting mixture was stirred at the same temperature for 3 hours. Insoluble material was filtered off, and the filtrate was concentrated under reduced pressure to give 0.5 g of (4R)-2-oxo-3-benzylthiazolidin-4-carbaldehyde as oily product. Physical properties of this product accorded to those of Reference Example 1-(4).

Reference Example 8

35.34 g of the compound obtained in Example 5, 121 ml of mesitylene and 116.1 g of methanesulfonic acid were heated at an inner temperature of 130° C. By setting a reaction starting time when the mixture reached to 125° C., the mixture was stirred at 128° C. to 133° C. for 4 hours, disappearance of monobenzylbiotin was confirmed by high performance liquid chromatography. The reaction mixture was cooled to 80° C., 30 ml of acetic acid was added thereto, and methanesulfonic acid layer was added dropwise to 710 ml of purified water. The mesitylene layer was separated, ice-cooled for 1 hour, and then, crude crystal was collected by filtration, and washed with 200 ml of water, and then, with methanol until black color of the washed solution disappeared. The crystal was dried at 50° C. by blowing air overnight to give 15.89 g of crude (+)-biotin.

The obtained crude (+)-biotin was dissolved in an aqueous solution comprising 160 ml of purified water containing 2.73 g of sodium hydroxide, and a pH of the solution was adjusted to 7 by using dil. hydrochloric acid at 90° C. to 95° C. At 90° C. to 95° C., 4 g of carbon powder was added into the system, and after stirring the mixture for 10 minutes, carbon powder precoate filtration was carried out. The filtrate was heated to 90° C. to 95° C. again, and 4 g of powder was again added to the system, and after the mixture was stirred for 10 minutes, the carbon coate precoat was filtered off. The filtrate was heated to 80° C. to 85° C. again, and a pH of the mixture was adjusted to 1.8 to 2.2 with conc. hydrochloric acid, and neutralization crystallization were carried out. The mixture was stirred at the same temperature for 1 hour to grow crystal. The mixture was gradually cooled, ice-cooled and then the crystal was collected by filtration. The crystal was dried by blowing air at 50° C. overnight to give 13.86 g of (+)-biotin as colorless crystal.

INDUSTRIAL APPLICABILITY

The process for preparing biotin of the present invention which uses Compound (IV) as a synthetic intermediate or the process for preparing biotin which uses Compound (I) and Compound (III) prepared by the processes of the present invention as a synthetic intermediate can produce biotin inexpensively as compared to the conventionally known processes mentioned in literatures, so that they become industrially advantageous processes of biotin.

The invention claimed is:

1. A process for preparing a compound represented by the formula (I):

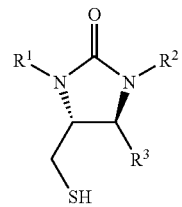

wherein $R^1$ and $R^2$ are the same or different from each other, and each represents a hydrogen atom, a benzyl group optionally having a substituent(s) on the benzene ring, a benzhydryl group optionally having a substituent(s) on the benzene ring, or a trityl group;

$R^3$ represents a cyano group, a carboxyl group, an alkoxycarbonyl group, an alkylthiocarbonyl group, or a carbamoyl group optionally having a substituent, or a salt thereof;

said method comprising:

subjecting a compound represented by the formula (II-a) or a salt thereof to ring transformation by reacting the compound at 0° C. to 200° C.:

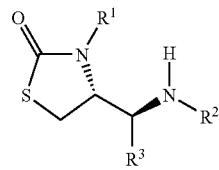

wherein the symbols have the same meanings as defined above;

thereby producing the compound of formula (I).

2. The process according claim 1, wherein the ring transformation proceeds at 80° C. to 100° C.

3. The process according to any one of claims 1 and 2, wherein $R^1$ and $R^2$ are the same or different, and each represents (1) hydrogen atom, (2) a benzyl group in which the benzene ring is optionally substituted by a group(s) selected from the group consisting of a halogen atom, an alkyl group and an alkoxy group, (3) a benzhydryl group in which the benzene ring is optionally substituted by a group(s) selected from the group consisting of a halogen atom, an alkyl group and an alkoxy group, or (4) a trityl group in which the benzene ring is optionally substituted by a group(s) selected from the group consisting of a halogen atom, an alkyl group and an alkoxy group, and $R^3$ is (1) cyano group, (2) carboxyl group, (3) an alkoxycarbonyl group, (4) an alkylthiocarbonyl group, or (5) a carbamoyl group optionally substituted by an alkyl group.

4. The process according to any one of claims 1 and 2, wherein $R^1$ and $R^2$ both represent benzyl groups, benzhydryl groups or trityl groups, and $R^3$ represents a carboxyl group, an alkoxycarbonyl group or a carbamoyl group.

* * * * *